United States Patent [19]

Krafton

[11] Patent Number: 4,499,069
[45] Date of Patent: Feb. 12, 1985

[54] ANTIPERSPIRANT EMULSION

[75] Inventor: Thomas J. Krafton, South Hampton, N.H.

[73] Assignee: The Gillette Company, Boston, Mass.

[21] Appl. No.: 464,663

[22] Filed: Feb. 7, 1983

[51] Int. Cl.³ .......................... A61K 7/32; A61K 7/38
[52] U.S. Cl. .......................................... 424/66; 424/68
[58] Field of Search ............................. 424/65, 68, 66

[56] References Cited

U.S. PATENT DOCUMENTS

| | | | |
|---|---|---|---|
| 4,122,029 | 10/1978 | Gee et al. | 252/308 |
| 4,264,586 | 4/1981 | Callingham et al. | 424/68 |
| 4,268,499 | 5/1981 | Keil | 424/68 |
| 4,350,605 | 9/1982 | Hughett | 424/68 |

FOREIGN PATENT DOCUMENTS 2018590  10/1979  United Kingdom ................. 424/68

OTHER PUBLICATIONS

Bulletin of ICI Americas Inc., entitled "Antiperspirants: Functionality and Benefits of ICI Americas' Surfactants and Emollients," 1980.

Primary Examiner—Dale R. Ore
Attorney, Agent, or Firm—Mandel E. Slater

[57] ABSTRACT

A stable antiperspirant emulsion is disclosed which contains an antiperspirant salt of aluminum and/or zirconium, volatile cyclic silicone, water, and a low pH-stable emulsifier mixture of polyethylene glycol (21) stearyl ether and a lipophilic co-emulsifier such that the HLB of the emulsifier mixture is more than 7.5 and less than 9.9.

15 Claims, No Drawings

ANTIPERSPIRANT EMULSION

BACKGROUND OF THE INVENTION

1. Field of the Invention

This invention relates to antiperspirant emulsions and more particularly to stable antiperspirant emulsions containing major portions of volatile cyclic silicone, water, and antiperspirant salts.

2. Description of the Prior Art

Antiperspirant compositions adapted for roll-on application which have achieved substantial consumer acceptance include such compositions as are described, for example, in British patent application No. GB 2018590 A. Such compositions are substantially anhydrous and comprise a powdered antiperspirant agent suspended in a liquid hydrophobic volatile silicone vehicle (generally 60 to 95% by weight) which includes a hydrophobic suspending agent, the composition containing less than 4% of other hydrophobic liquids which are less volatile than the cyclic silicone. These compositions have excellent "feel," are neither sticky nor tacky, apply smoothly, and dry quickly.

Having achieved these desirable properties, it would nevertheless be avantageous to the formulator to reduce the cost of the composition described above by replacing the expensive volatile cyclic silicone, or at least a major portion thereof, with water, while at the same time avoiding a sacrifice of the above-mentioned desired properties. This goal might be achieved by retaining some of the silicone, for the quick drying and good "feel" it affords to the product, while providing a stable emulsion with a major portion of water, in the presence of the antiperspirant ingredient.

Such an approach has been proposed, for example, in a publication of the Product Development Department of ICI Americas Inc., entitled "Antiperspirants: Functionality and Benefits of ICI Americas' Surfactants and Emollients" (1980), wherein at page 32 it is proposed to emulsify a quick-drying aluminum chlorhydroxide antiperspirant lotion including volatile cyclic silicone and water with a surfactant mixture of polyethylene glycol (2) cetyl ether and polyethylene glycol (23) lauryl ether, which surfactants are present in a ratio of 3.4:1 and together account for 4% by weight of the total composition. Although the volatile silicone requires HLB 8 and the surfactant mixture described can be shown to have HLB32 7.9, the emulsion is not stable. Further attempts to create a stable antiperspirant emulsion of volatile cyclic silicone and water, using a surfactant mixture at HLB 8 of polyethylene glycol (20) stearyl ether or polyethylene glycol (20) cetyl ether, together with polyethylene glycol (2) stearyl ether, also were not successful.

SUMMARY OF THE INVENTION

Accordingly, it is an object of the invention to provide an antiperspirant composition in which the advantages associated with volatile cyclic silicones are maintained while substituting an inexpensive replacement for a major portion thereof.

A further and more specific object of the invention is to provide a stable antiperspirant emulsion including volatile cyclic silicone, water, and antiperspirant salts.

With the above objects in view, according to the present invention there is provided a stable antiperspirant emulsion in which, unexpectedly, a surfactant mixture containing polyethylene glycol (21) stearyl ether affords excellent stability, while as indicated previously, the closely-related polyethylene glycol (20) stearyl ether does not. Stable antiperspirant emulsions according to the invention include from about 5% to about 25% of an antiperspirant salt of aluminum or zirconium or combinations thereof, from about 15% to about 25% of a volatile cyclic silicone from about 2% to about 10% of a low pH-stable emulsifier mixture which comprises polyethylene glycol (21) stearyl ether and a lipophilic co-emulsifier such that the HLB of the emulsifier mixture is more than 7.5 and less than 9.9, and from about 35% to about 78% water, the percentages being by weight based on the total weight of the composition. Optionally the composition may include up to about 3% of a low pH-stable emollient capable of reducing the tackiness associated with antiperspirant salts, and up to about 3% of an oil-absorbing material.

DESCRIPTION OF THE PREFERRED EMBODIMENTS

The antiperspirant salts of aluminum and/or zirconium may be selected from the various materials of this nature available. Suitable such materials are, for example, aluminum chloride, aluminum chlorhydroxide, basic aluminum bromide, zirconyl chloride, zirconyl hydroxide, complexes of aluminum hydroxide, zirconyl chloride and aluminum chlorhydroxide, complexes of aluminum hydroxide, zirconyl hydroxychloride and aluminum chlorhydroxide, complexes of dihydroxyaluminum glycinate, zirconyl chloride and/or zirconyl hydroxychloride and aluminum chlorhydroxides, complexes of zirconyl chloride and/or zirconyl hydroxychloride with aluminum chlorhydroxide and an amino acid, such as glycine (as a buffering agent), and mixtures of two or more of the above. The antiperspirant used is generally soluble in water, but insoluble in the volatile cyclic silicone, which is hydrophobic. The amount of antiperspirant present may be varied to suit particular needs. In general, the compositions will comprise from about 5 to 25% antiperspirant by weight, and preferably from about 15 to 20% by weight, of the composition. There must be enough of the active material present for the composition to be effective as an antiperspirant. On the other hand it is expected that concentrations above about 20-25% of the antiperspirant salt will be outside regulatory limits. (As used herein these antiperspirant salt concentrations are based upon equivalent amounts of the particular hydrated salt.) A particularly effective antiperspirant salt, designated according to its Cosmelic, Toiletry and Fragrance Association (CTFA) adopted name, is aluminum zirconium tetrachlorohydrex gly, which is a coordination complex of aluminum zirconium tetrachlorohydrate and glycine in which some of the water molecules normally coordinated to the metals have been displaced by the glycine. This material is available commercially from Wickhen Products under the designation WICKENOL 368, 369, or 374.

The volatile cyclic silicones which are used in the composition of the present invention are well known and have been generally taught to be useful in antiperspirant formulations. Generally such volatile cyclic silicones may be represented by the formula:

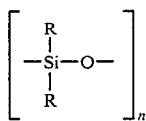

wherein R is a 1 to 3 carbon alkyl group, n is a number from 3 to 10, preferably from 3 to 7, and the unsatisfied valences on the oxygen and silicon atoms at the ends of the chain are joined to one another to form a cyclic structure. Suitable volatile cyclic silicones are, for example, (a) U.C.C. Y-7207 sold by Union Carbide Corporation in which each R is methyl and which typically comprises by weight 99.4% tetramer, 0.6% trimer and traces of the pentamer and hexamer; (b) SWS-03314 (sold by SWS Silicones, a Division of Stauffer Chemical Company) in which R is methyl and which is substantially all tetramer; and (c) Dow Corning 344 fluid in which R is methyl and which typically comprises by weight about 88% tetramer, about 11.8% pentamer and traces of trimer and hexamer.

Typical vapor pressures of the volatile cyclic silicones are shown in Table 1 below wherein the vapor pressures for Dow Corning 344 fluid at various temperatures are set forth.

TABLE 1

| Temperature | Vapor Pressure, mmHg |
|---|---|
| 26° C. | 1 |
| 64° C. | 10 |
| 77° C. | 20 |
| 92° C. | 40 |
| 101° C. | 60 |
| 114° C. | 100 |
| 155° C. | 400 |
| 178° C. | 760 |

In compositions according to the present invention the amount of volatile cyclic silicone will be reduced as much as practicable from the amounts disclosed in the above-mentioned British patent application No. GB 2018590 A, in order to realize maximum cost savings, but not so much as to sacrifice the pleasant feel and quick drying properties afforded by its use. According to the invention, the compositions will preferably contain from about 15% to about 25% of the volatile cyclic silicone; 18% to 22% gave particularly good results.

The emulsifer mixture, as previously indicated, includes polyethylene glycol (21) stearyl ether as the critical component. This material may be defined as the glycol ether of stearyl alcohol that conforms to the formula $CH_3(CH_2)_{16}(OCH_2CH_2)_nOH$ where n has an average value of 21. It is available from ICI Americas under the name BRIJ 721 and, as an ether-linked ethoxylate, is quite stable in the acid pH environment characteristic of the antiperspirant salts. It has HLB=15.5 and so is combined with an acid-stable lipophilic co-emulsifier in order to achieve HLB greater than 7.5 and less than 9.9, the range preferred according to the present invention, the range 7.8 to 8.2 being especially preferred. Since, as indicated, acid stability is required of the co-emulsifier, another ether-linked ethoxylate is a preferred choice, with polyethylene glycol (2) stearyl ether being especially preferred. Examples of the latter material include BRIJ 72, sold by ICI Americas, Volpo S.2, sold by Croda, and Lipocol S-2, sold by Lipo Chemicals. At least about 2% of the emulsifier mixture is required to obtain a stable emulsion of water and volatile cyclic silicone (and other oily material) in the presence of the antiperspirant salt. More than about 5% is unnecessary and would also tend to give the composition a greasy feel and might make it too viscous to use as a roll-on antiperspirant. However such compositions with higher concentration of emulsifier could be useful in other application forms such as creams, in which case up to about 10% of the emulsifier mixture might be used. Particularly preferred for a roll-on product is an emulsifier mixture concentration of 2.5% to 4%.

Compositions according to the present invention may optionally contain additional ingredients to reduce tackiness and any oily or greasy feel. Certain low pH-stable emollients are found to have the ability to reduce the tackiness associated with antiperspirant salts, a particularly effective example of such a material being polypropylene glycol (15) stearyl ether, which is the polypropylene glycol ether of stearyl alcohol according to the formula

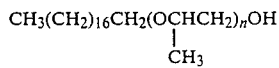

where n has an average value of 15. This material may be obtained, for example, from ICI Americas under the designation ARLAMOL E or from Heterene Chemical Company as HETOXOL SP-15. The emollient, if present, is preferably used at a concentration of about 1% to 3% of the total composition, with a concentration of 1.5% to 2% most preferred. Excess oiliness may be reduced by the use of up to 3%, preferably 1% to 3%, and more preferably 1.5% to 2.5%, of an oil-absorbent material, aluminum starch octenylsuccinate (available from National Starch under the name "Dry Flo") being a representative example of such a material.

In addition to the above-described ingredients small quantities of such additional materials as preservatives and a perfume may also be present.

In order that the invention may be more fully understood, the following examples are given by way of illustration only. All parts and percentages are by weight.

Two antiperspirant formulations were made up comprising the following ingredients:

| | | % by Weight | |
|---|---|---|---|
| | Ingredient | Formulation A | Formulation B |
| 1. | Dow Corning 344 Silicone | 20.00 | 20.00 |
| 2. | Brij 72 | 2.20 | 2.20 |
| 3a. | Polyethylene Glycol (21) Stearyl Ether | 1.00 | — |
| 3b. | Polyethylene Glycol (20) Stearyl Ether | — | 1.00 |
| 4. | Arlamol E | 1.80 | 1.80 |
| 5. | Aluminum Starch Octenylsuccinate | 2.00 | 2.00 |
| 6. | Butylparaben | 0.15 | 0.15 |
| 7. | Aluminum Zirconium Tetrachlorohydrex Gly, 35% Aqueous Solution | 57.10* | 57.10* |
| 8. | Deionized Water | 15.65** | 15.65** |
| 9. | Methylparaben | 0.10 | 0.10 |

*Corresponds to 20% by weight of the hydrated salt.
**Total water is 52.75% by weight.

The oil phase ingredients (1–6) were mixed at 70° C. and the water phase ingredients (7–9) mixed at 72° C. Then the aqueous phase was added to the oil phase at about 70° C. with low-shear mixing until homogeneous, taking care not to whip air into the emulsion.

Stability of each emulsion was tested by filling it into a 250 ml wide-mouth jar, capping, and storing at 45° C., checking the appearance of the jar contents at regular intervals for emulsion separation. After four weeks of storage under the above conditions Formulation A had developed a small (2-3 mm) mostly water layer at the bottom containing a small amount of starch, with the remainder a milky liquid into which the small water layer was easily redispersed. After the same interval Formulation B, by contrast, showed extreme separation of the oil and water phases with, from the bottom, 2-3 mm starch, about 30 mm of a water phase layer, about 30 mm of an oil phase layer, and on top about 2-3 mm of another oil layer, mostly silicone; and vigorous shaking would not redisperse the contents.

Additional antiperspirant formulations were prepared similar to Formulation A, varying the proportions of polyethylene glycol (21) stearyl ether and Brij 72, adjusting only the water to maintain the total of all ingredients at 100%:

|  | Polyethylene Glycol (21) Stearyl Ether | Brij 72 | HLB |
| --- | --- | --- | --- |
| Formulation C | 1.60% | 1.80% | 9.9 |
| Formulation D | 1.30 | 1.50 | 9.8 |
| Formulation E | 1.40 | 1.60 | 9.9 |
| Formulation F | 1.50 | 1.70 | 9.9 |
| Formulation G | 1.56 | 3.44 | 8.2 |
| Formulation H | 2.50 | 5.50 | 8.2 |

After four weeks of storage under the conditions described above, Formulations C-F all developed about a one-inch separated layer, which while easily redispersed on shaking, may be considered only borderline acceptability. Formulation G under the same conditions developed virtually no separation (less than ½ mm layer at the bottom, which easily redispersed) and had a viscosity of 7000 cps, somewhat viscous but still acceptable for roll-on application. Formulation H exhibited no separation and was in the form of a smooth off-white cream, having a viscosity of about 25,000 cps shortly after preparation and rising gradually to and stabilizing at about 30,000 cps.

What is claimed is:

1. A stable antiperspirant emulsion consisting essentially of:
   (a) from about 5% to about 25% of an antiperspirant salt of aluminum or zirconium or combinations thereof,
   (b) from about 15% to about 25% of a volatile cyclic silicone,
   (c) from about 2% to about 10% of a low pH-stable emulsifier mixture which comprises polyethylene glycol (21) stearyl ether and a lipophilic co-emulsifier such that the HLB of the emulsifier mixture is more than 7.5 and less than 9.9, and
   (d) from about 35% to about 78% of water, said percentages being by weight based on the total weight of the composition.

2. The antiperspirant emulsion of claim 1, further including up to about 3% of a low pH-stable emollient adapted to reduce antiperspirant salt tackiness.

3. The antiperspirant emulsion of claim 1, further inlcuding up to about 3% of an oil-absorbing material.

4. The invention of claim 1 wherein said lipophilic co-emulsifier is polyethylene glycol (2) stearyl ether.

5. The invention of claim 4 wherein said emulsifier mixture comprises from about 2.5% to about 4.0% of the total composition.

6. The invention of claim 1 wherein the HLB of the emulsifier mixture is from 7.8 to 8.2.

7. The invention of claim 1 wherein the volatile cyclic silicone comprises from about 18% to about 22% of the total composition.

8. The invention of claim 2 wherein said emollient comprises from about 1% to about 3% of the total composition.

9. The invention of claim 2 wherein said emollient comprises from about 1.5% to about 2% of the total composition.

10. The invention of claim 8 wherein said emollient is polypropylene glycol (15) stearyl ether.

11. The invention of claim 3 wherein said oil-absorbing material comprises from about 1% to about 3% of the total composition.

12. The invention of claim 3 wherein said oil-absorbing material comprises from about 1.5 to about 2.5% of the total composition.

13. The invention of claim 11 wherein said oil-absorbing material is aluminum starch octenylsuccinate.

14. The invention of claim 1 wherein said antiperspirant salt comprises from about 15% to about 20% of lhe total composition.

15. A stable antiperspirant emulsion comprising:
   (a) from about 15% to about 20% of an antiperspirant salt of aluminum or zirconium or combinations thereof,
   (b) from about 18% to about 22% of a volatile cyclic silicone,
   (c) from about 2.5% to about 4.0% of a low pH-stable emulsifier mixture which comprises polyethylene glycol (21) stearyl ether and polyethylene glycol (2) stearyl ether such that the HLB of the emulsifier mixture is from 7.8 to 8.2,
   (d) from about 1.5% to about 2.0% of polypropylene glycol (15) stearyl ether,
   (e) from about 1.5% to about 2.5% of aluminum starch octenylsuccinate, and
   (f) from about 45% to about 63% water.

* * * * *

UNITED STATES PATENT AND TRADEMARK OFFICE
CERTIFICATE OF CORRECTION

PATENT NO. : 4,499,069
DATED : February 12, 1985
INVENTOR(S) : Thomas J. Krafton It is certified that error appears in the above-identified patent and that said Letters Patent is hereby corrected as shown below:

Column 3, line 53, change "$CH_3(CH_2)_{16}(OCH_2CH_2)_nOH$"

to -- $CH_3(CH_2)_{16}CH_2(OCH_2CH_2)_nOH$ --.

Signed and Sealed this

Tenth Day of June 1986

[SEAL]

Attest:

DONALD J. QUIGG

Attesting Officer

Commissioner of Patents and Trademarks